(12) United States Patent
Tanaka et al.

(10) Patent No.: US 8,158,694 B2
(45) Date of Patent: *Apr. 17, 2012

(54) SINGLE COMPONENT DENTAL COMPOSITION CONTAINING SILANE COUPLING AGENT AND ACIDIC GROUP CONTAINING POLYMERIZABLE MONOMER

(75) Inventors: Hisaki Tanaka, Kyoto (JP); Toshihide Fujii, Kyoto (JP); Yutaka Yamaguchi, Kyoto (JP); Mikito Deguchi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/008,174

(22) Filed: Jan. 18, 2011

(65) Prior Publication Data

US 2011/0112209 A1    May 12, 2011

Related U.S. Application Data

(63) Continuation of application No. 12/312,243, filed as application No. PCT/JP2007/071401 on Nov. 2, 2007, now abandoned.

(30) Foreign Application Priority Data

Nov. 2, 2006   (WO) .................. PCT/JP2006/321989

(51) Int. Cl.
    *A61K 6/00*   (2006.01)
    *A61K 6/083*  (2006.01)

(52) U.S. Cl. ........... 522/79; 522/171; 522/172; 523/118

(58) Field of Classification Search ............. 522/79, 522/171, 172; 523/118
    See application file for complete search history.

(56) References Cited

U.S. PATENT DOCUMENTS

| | | | |
|---|---|---|---|
| 4,499,251 A * | 2/1985 | Omura et al. ............... | 526/278 |
| 4,539,382 A | 9/1985 | Omura et al. | |
| 4,872,936 A | 10/1989 | Engelbrecht | |
| 5,321,053 A | 6/1994 | Hino et al. | |
| 5,530,038 A | 6/1996 | Yamamoto et al. | |
| 5,670,657 A | 9/1997 | Kojima et al. | |
| 5,707,611 A | 1/1998 | Ikemura et al. | |
| 5,849,813 A | 12/1998 | Oxman | |
| 5,925,690 A | 7/1999 | Fuchigami et al. | |
| 6,174,935 B1 * | 1/2001 | Matsunae et al. ............. | 523/118 |
| 6,288,138 B1 | 9/2001 | Yamamoto et al. | |
| 6,900,251 B2 | 5/2005 | Moszner et al. | |
| 7,776,936 B2 * | 8/2010 | Tanaka et al. .................. | 522/79 |
| 7,879,924 B2 * | 2/2011 | Torii et al. .................... | 523/116 |
| 8,029,613 B2 * | 10/2011 | Tanaka et al. .................. | 106/35 |
| 2007/0100020 A1 * | 5/2007 | Nakatsuka et al. ........... | 523/118 |
| 2009/0023856 A1 * | 1/2009 | Nakatsuka et al. ........... | 524/544 |
| 2010/0112362 A1 * | 5/2010 | Craciun et al. ............... | 428/458 |
| 2010/0240796 A1 * | 9/2010 | Bock et al. .................... | 523/118 |

FOREIGN PATENT DOCUMENTS

| | | |
|---|---|---|
| JP | 2001-72936 | 3/2001 |
| JP | 2002-38105 | 2/2002 |
| JP | 2003-13012 | 1/2003 |
| JP | 2006-45179 | 2/2006 |

OTHER PUBLICATIONS

Machine translation from PAJ website of JP Publication No. 07-277913, Oct. 24, 1995.*
Abstratc of JP Publication No. 07-277913, Oct. 24, 1995.*
International Search Report dated Jan. 22, 2008 in the International (PCT) Application PCT/JP2007/071401 of which the parent application is the U.S. National Stage.
International Preliminary Report on Patentability including English Translation of PCT Written Opinion dated Jun. 4, 2009 in the International (PCT) Application PCT/JP2007/071401 of which the parent application is the U.S. National Stage.

* cited by examiner

*Primary Examiner* — Susan W Berman
(74) *Attorney, Agent, or Firm* — Wenderoth, Lind & Ponack, L.L.P.

(57) ABSTRACT

The present invention provides a one-component dental adhesive composition which can exhibit excellent adhesion to both materials of a dental ceramics and an organic composite containing an inorganic compound, and is excellent in can-stability. More particularly, the present invention provides a one-component dental adhesive composition comprising 1 to 60 parts by weight of (a) a silane coupling agent, 1.0 to 20.0 parts by weight based on 100 parts by weight of the (a) component of (b) an acidic group-containing polymerizable monomer, and 28 to 99 parts by weight of (c) a volatile organic solvent.

2 Claims, No Drawings

SINGLE COMPONENT DENTAL COMPOSITION CONTAINING SILANE COUPLING AGENT AND ACIDIC GROUP CONTAINING POLYMERIZABLE MONOMER

This application is a Continuation of U.S. application Ser. No. 12/312,243, filed May 1, 2009 now abandoned, which is a national stage application of International application No. PCT/JP2007/071401, filed Nov. 2, 2007.

TECHNICAL FIELD

The present invention is a single-component dental adhesive composition which exhibits excellent adhesion to both materials of a dental ceramics and an organic composite containing an inorganic compound (hereinafter, referred to as composite material in some cases), and is excellent in can-stability.

BACKGROUND ART

In a restorative dental material, inorganic materials, and composites of inorganic-organic composite materials are used in many cases, a representative of which is a dental porcelain (main component is silicon dioxide), an alumina core, a zirconia core, and a composite. The composite is obtained by mixing an inorganic powder and a resin into a paste. Alternatively, metal materials are also used.

Previously, in adhesion of them, there was a trial to improve adhesion of a surface using a silane coupling agent, and a trial to improve adhesion of a surface using an acidic monomer. The silane coupling agent is known to improve adhesion to a material containing silicon dioxide as a main component, and the acidic monomer is known to improve adhesion to a material containing alumina and zirconia as a main component.

However, since in the dental restorative material, silica-based, alumina-based, zirconia-based and metal-based materials are used as described above, it is necessary to select an adhesive, and perform coating in conformity with an adherend.

In recent years, in order to overcome these problems, an adhesive containing both of a silane coupling agent and an acidic monomer has been sold. However, usually, since the silane coupling agent and the acidic monomer can not be preserved in the same solvent for a long period of time, two kinds of materials must be used by mixing them immediately before use.

A material which can be used regardless of a kind of an adherend, and does not need a labor such as mixing before use, has been sought.

JP-A No. 63-51308 and JP-A No. 7-277913 disclose a dental adhesive composition for adhering a dental porcelain containing silicon dioxide, and a dental restorative material such as a dental resin, a dental alloy and the like by combining a silane coupling agent and a phosphoric acid ester monomer.

However, it is difficult that the silane coupling agent and the acidic monomer coexist, and they must be mixed before use.

In addition, JP-A No. 9-137129 discloses a dental adhesive composition obtained from a coating material consisting of a coating solution containing a silane coupling agent and an acidic compound such as organic carboxylic acid and the like, and a polymerizable monomer which is coated on coating surface of the coating solution and is polymerized in the presence of a polymerization catalyst, but since this dental adhesive composition has little adhesion to aluminum oxide and zirconium oxide, it is necessary to select an adherend.

JP-A No. 2006-45179 discloses a dental adhesive composition for adhering a dental material consisting of an inorganic compound, or an organic composite containing an inorganic compound, and a dental adhesive composition having adhesion to aluminum oxide and zirconium oxide is proposed.

However, a silane coupling agent is deteriorated by a phosphonic acid group-containing (meth)acrylate-based monomer, and it is difficult to stably exhibit the adhering effect for a long period of time. And, it is difficult that the silane coupling agent and the acidic monomer coexist, and they must be mixed before use.

JP-A No. 2006-45094 describes a two-component mixed type primer composition for improving adhesiveness by pre-treating a surface to be adhered of a prosthesis consisting of a cured dental composite material before application of the adhering material upon adhesion of a cured product of a dental composite material and a dental material. However, this adhesive has no adhesion to a porcelain, and has a primer composition such that two components must be mixed before adhesion.

JP-A No. 2000-248201 discloses a composition which exhibits sufficient adhesion to any of a base metal alloy, a noble alloy, and a ceramics, but when a silane coupling agent and an acidic group-containing polymerizable polymer are used as a single-component composition, a serious defect arises regarding can-stability of the single-component composition.

JP-A No. 2002-265312 discloses the technique of composition which exhibits sufficient adhesion to any of a tooth substance, a base metal alloy, a noble metal alloy, and a ceramics, but when a silane coupling agent and an acidic group-containing polymerizable monomer are used as a single-component composition, a serious defect arises regarding can-stability of the single-component composition.

Patent Publication 1: JP-A No. 63-51308
Patent Publication 2: JP-A No. 7-277913
Patent Publication 3: JP-A No. 9-137129
Patent Publication 4: JP-A No. 2006-45179
Patent Publication 5: JP-A No. 2006-45094
Patent Publication 6: JP-A No. 2000-248201
Patent Publication 7: JP-A No. 2000-265312

DISCLOSURE OF THE INVENTION

Problems to be Solved by the Invention

An object of the present invention is to exhibit excellent adhesion to both materials of a dental ceramics and an organic composite containing an inorganic compound. Particularly, an object of the present invention is to respond to demand of a material having an improved adhesive power with a single-component, without selecting silica-based, alumina-based, zirconia-based, and metal-based materials.

A further object is to provide a dental adhesive composition having good handling property which is mostly desired by users for the purpose of shortening a working time, reducing a technical error or the like, that is, provide a single-component dental adhesive composition.

The present invention responds to demand of a single-component dental adhesive composition prepared by formulating a silane coupling agent and an acidic group-containing polymerizable monomer into the same solution. As used herein, the single-component dental adhesive composition is typified by a dental primer, a dental adhesive, and a dental adhesive restorative material.

Means to Solve the Problems

The present invention was done in order to solve the aforementioned problems, and is a single-component dental adhesive composition comprising 1 to 60 parts by weight of (a) a silane coupling agent, 1.0 to 20.0 parts by weight based on 100 parts by weight of the (a) component of (b) an acidic group-containing polymerizable monomer, and 28 to 99 parts by weight of (c) a volatile organic solvent.

The present invention is a one-component dental primer comprising (a) a silane coupling agent, (b) an acidic group-containing polymerizable monomer, and (c) a volatile organic solvent, wherein the dental primer comprises 1 to 60 parts by weight of (a) a silane coupling agent, 1.0 to 20.0 parts by weight based on 100 parts by weight of the (a) component of (b) an acidic group-containing polymerizable monomer, and 28 to 99 parts by weight of (c) a volatile organic solvent.

The present invention is a one-component dental primer comprising (a) a silane coupling agent, (b) an acidic group-containing polymerizable monomer, and (c) a volatile organic solvent, wherein the (b) acidic group-containing polymerizable monomer is a phosphonic acid group-containing (meth)acrylate-based monomer, and the phosphonic acid group-containing (meth)acrylate-based monomer is represented by the following general formula (I):

[Chemical Formula 1]

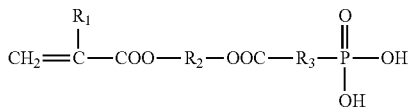

[1]

(wherein $R_1$ denotes a hydrogen atom or a methyl atom, $R_2$ denotes an alkylene group of a carbon number of 1 to 20 optionally having a substituent, and $R_3$ denotes an alkylene group of a carbon number of 1 to 15 optionally having a substituent).

The present invention is a one-component dental adhesive comprising a radical polymerizable monomer, (a) a silane coupling agent, (b) an acidic group-containing polymerizable monomer, and a photopolymerization initiator, wherein (b) the acidic group-containing polymerizable monomer is 1.0 to 20.0 parts by weight based on 100 parts by weight of (a) the silane coupling agent.

The present invention is a one-component dental adhesive comprising a radical polymerizable monomer, (a) a silane coupling agent, (b) an acidic group-containing polymerizable monomer, and a photopolymerization initiator, wherein (b) the acidic group-containing polymerizable monomer is a phosphonic acid group-containing (meth)acrylate-based monomer, and the phosphonic acid group-containing (meth)acrylate-based monomer is represented by the following general formula (I):

[Chemical Formula 2]

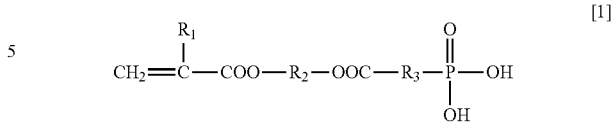

[1]

(wherein $R_1$ denotes a hydrogen atom or a methyl atom, $R_2$ denotes an alkylene group of a carbon number of 1 to 20 optionally having a substituent, and $R_3$ denotes an alkylene group of a carbon number of 1 to 15 optionally having a substituent).

The present invention is a one-component dental adhesive restorative material comprising a radical polymerizable monomer, (a) a silane coupling agent, (b) an acidic group-containing polymerizable monomer, a photopolymerization initiator, and a filler, wherein (b) the acidic group-containing polymerizable monomer is 1.0 to 20.0 parts by weight based on 100 parts by weight of (a) the silane coupling agent.

The present invention is a one-component dental adhesive restorative material comprising a radical polymerizable monomer, (a) a silane coupling agent, (b) an acidic group-containing polymerizable monomer, a photopolymerization initiator, and a filler, wherein (b) the acidic group-containing polymerizable monomer is a phosphonic acid group-containing (meth)acrylate-based monomer, and the phosphonic acid group-containing (meth)acrylate-based monomer is represented by the following general formula (I):

[Chemical Formula 3]

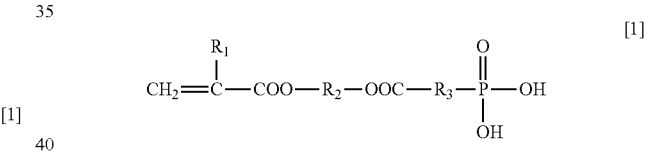

[1]

(wherein $R_1$ denotes a hydrogen atom or a methyl atom, $R_2$ denotes an alkylene group of a carbon number of 1 to 20 optionally having a substituent, and $R_3$ denotes an alkylene group of a carbon number of 1 to 15 optionally having a substituent).

Adoption of such the construction results in excellent adhesiveness and durability on each of a dental ceramics, and an organic composite containing an inorganic compound, which has not previously been seen, and handling is simple, and can-stability is excellent.

And, (a) the silane coupling agent is characterized by being represented by the following general formula [2].

[Chemical Formula 4]

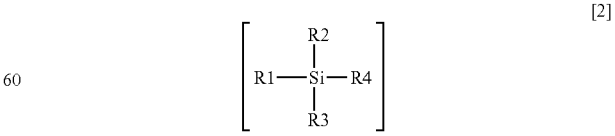

[2]

(In the above formula, $R_1$ represents an organic residue having at least one functional group selected from the group consisting of a (meth)acryloyl group, a vinyl group, a styryl group, a mercapto group, and an epoxy group, $R_2$ represents a hydroxy group, an alkyl group of a carbon number of 1 to 5 or an alkoxy group of a carbon number of 1 to 5, and $R_3$ and $R_4$ each represent a hydroxy group or an alkoxy group of a carbon number of 1 to 5)

A preferable (a) silane coupling agent is a compound in which, in the general formula [2], $R_1$ is an organic residue having at least one functional group selected from the group consisting of a (meth)acryloyl group, and a vinyl group, $R_2$ is a hydroxy group, an alkyl group of a carbon number of 1 to 5 or an alkoxy group of a carbon number of 1 to 5, and $R_3$ and $R_4$ each are a hydroxy group or an alkoxy group of a carbon number of 1 to 5.

And, (b) the acidic group-containing polymerizable monomer is characterized in that it is 4-(meth)acryloxyethyltrimellitic acid, 4-(meth)acryloxyethyltrimellitic acid anhydride, 6-(meth)acryloxyhexyl phosphonoacetate, 6-(meth)acryloxyhexyl phosphonopropionate, or 10-(meth)acryloxydecyl hydrogen phosphate.

And, (c) the volatile organic solvent is characterized in that it is methanol, ethanol, isopropanol, butanol, acetone, ethyl acetate, isopropyl ether, or a radical-polymerizable monomer such as (meth)acrylic acid ester, (meth)acrylamide, vinyl ester or the like.

Effect of the Invention

By using the dental adhesive composition of the present invention, excellent adhesiveness and durability can be exhibited on both materials of a dental ceramics, and an organic composite containing an inorganic compound and, further, can-stability is excellent, and handling is simple. Particularly, adhesion on silica-based, alumina-based and zirconia-based dental materials, and non-noble metals, and inorganic organic composites is excellent.

As specific utility of the dental adhesive composition of the present invention, the composition is used in adhesion with a resin-based material when any of a dental restoration/a dental restorative material/a dental device is a dental ceramics containing silicon dioxide as a main component, a dental ceramics containing aluminum dioxide and zirconium dioxide as a main component, a resin-based material containing a ceramics or an inorganic filler, or a dental restoration made of a non-metal material, in adhesion between any of a dental restoration/a dental restorative material/a dental device.

The dental adhesive restorative material is such that a dental restorative material itself is made to have adhesiveness using the technique of the present invention. Specifically, the material is an adhesive composite resin for a facing crown or fracture restoration.

By using the dental adhesive composition of the present invention, a dentist can simply implement an adhering work without selecting an adherend. In addition, a handling method is entirely the same as that of various adhesive compositions which have been used until now. That is, although the composition is an adhesive composition having essentially entirely new function, since the using method is the same, it is easily accepted by a dentist who is a user, and is advantageous to whole dental therapy.

Since the dental adhesive composition in the present invention is a one-component adhesive composition, handling is simple. In this regard, previously, since the composition was in a two-component mixed-type merchandise form, a mixing procedure was necessary upon use, a procedure was troublesome, working was time-consuming, and many points were unknown, as whether an appropriate mixing ratio of two components is maintained, and a sufficient mixing procedure has been done or not was unclear, and a technical error was easily generated, causing a loss.

The present invention can be also used as a primer, and can be also used simultaneously with other adhesive.

BEST MODE FOR CARRYING OUT THE INVENTION

A specific embodiment in the dental adhesive composition of the present invention is a single-component dental ceramics, a dental primer of an organic composite containing an inorganic compound, a dental adhesive, and a dental adhesive restorative material. An adhesive composite resin is included in a dental adhesive restorative material, and a resin cement is included in a dental adhesive.

Particularly, high adhesiveness can be exhibited by extremely simple treatment in use as a single-component dental primer of an organic composite containing a dental ceramics, or an inorganic compound.

The dental adhesive composition of the present invention, as its aspect, is excellent in use in a dental bonding agent which is a dental adhesive, an orthodontic adhesive, a resin cement, and a dual curing-type resin cement. Alternatively, as application to a dental adhesive restorative material, the composition can be used in an opaque agent, a compomer, a resin core, an adhesive composite resin, a facing crown material or the like.

It is preferable to use a silane coupling agent having a functional group which can be copolymerized with or form a chemical bond with a polymerizable monomer component in a dental adhesive composition and an adherend material, as (a) the silane coupling agent used in the present invention, in order to obtain good adhesion to a ceramics material.

In the present invention, as a silane coupling agent satisfying this condition, a silane compound represented by the general formula [2] is used. Among the functional group possessed by R1, a (meth)acryloyl group, a vinyl group, and a styryl group are connected to a polymer of (meth)acrylic acid ester monomer by copolymerization with a (meth)acrylic acid ester monomer, and a mercapto group is connected to a polymer of a (meth)acrylic acid ester monomer by formation of a chemical bond derived from a chain transfer/stopping reaction, and an epoxy group is connected to a polymer of a (meth)acrylic acid ester monomer by forming a chemical bond with a monomer having an amino group or a carboxyl group reactive therewith. In order to make condensation of a silane coupling agent and a silanol group on an adherend surface rapid, it is preferable that R2, R3 and R4 are each a lower alkoxy group of a carbon number of 1 to 5 or a hydroxy group, provided that R2 may be an alkyl group of a carbon number of 1 to 5.

Specific examples of the silane coupling agent satisfying the aforementioned condition include the following:

[Chemical Formula 5]

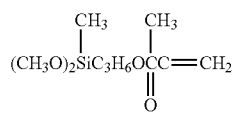

3-Methacryloxypropylmethyldimethoxysilane

[Chemical Formula 6]

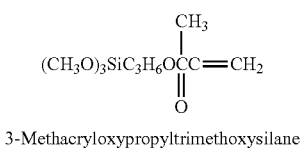

3-Methacryloxypropyltrimethoxysilane

[Chemical Formula 7]

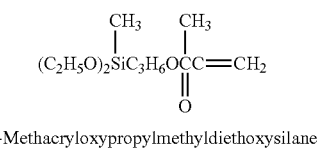

3-Methacryloxypropylmethyldiethoxysilane

[Chemical Formula 8]

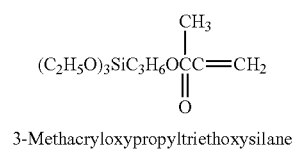

3-Methacryloxypropyltriethoxysilane

[Chemical Formula 9]

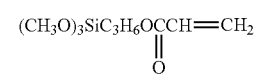

3-Acryloxypropyltrimethoxysilane

[Chemical Formula 10]

Vinyltrimethoxysilane

[Chemical Formula 11]

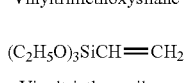

Vinyltriethoxysilane

[Chemical Formula 12]

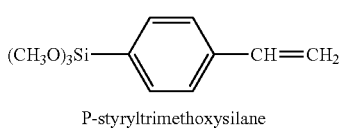

P-styryltrimethoxysilane

[Chemical Formula 13]

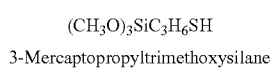

3-Mercaptopropyltrimethoxysilane

[Chemical Formula 14]

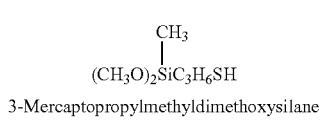

3-Mercaptopropylmethyldimethoxysilane

[Chemical Formula 15]

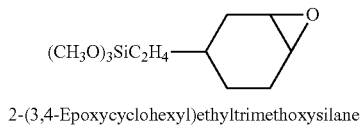

2-(3,4-Epoxycyclohexyl)ethyltrimethoxysilane

[Chemical Formula 16]

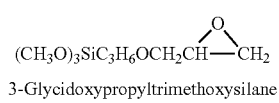

3-Glycidoxypropyltrimethoxysilane

[Chemical Formula 17]

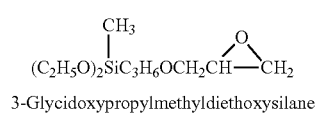

3-Glycidoxypropylmethyldiethoxysilane

[Chemical Formula 18]

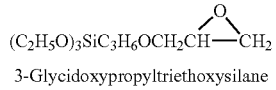

3-Glycidoxypropyltriethoxysilane

A preferable (a) silane coupling agent is a compound in which, in the general formula [2], $R_1$ is an organic residue having at least one functional group selected from the group consisting of a (meth)acryloyl group, and a vinyl group, $R_2$ is a hydroxy group, an alkyl group of a carbon number of 1 to 5 or an alkoxy group of a carbon number of 1 to 5, and $R_3$ and $R_4$ are each a hydroxy group or an alkoxy group of a carbon number of 1 to 5.

A particularly preferable (a) silane coupling agent is 3-methacryloxypropylmethyldimethoxysilane, 3-methacryloxypropyltrimethoxysilane, 3-methacryloxypropylmethyldiethoxysilane, 3-methacryloxypropyltriethoxysilane, and 3-acryloxypropyltrimethoxysilane.

A blending ratio of (a) the silane coupling agent may be appropriately used depending on the use purpose of the composition, and is adjusted in the range of 1 to 60 parts by weight, preferably adjusted in the range of 5.0 to 50 parts by weight.

As the acidic group-containing polymerizable monomer in the present invention, all polymerizable monomers which have previously been used as a dental acidic group-containing polymerizable monomer can be used and, particularly, monomers can be used by selecting from polymerizable monomers having a carboxyl group, a phosphoric acid ester group, a phosphonic acid group, a pyrophosphoric acid group, or a sulfonic acid group in the molecule.

Among the acidic group-containing polymerizable monomer in the present invention, examples of the monomer containing a carboxyl group in the molecule include methacrylic acid, 4-(meth)acryloxyethyltrimellitic acid, 4-(meth) acryloyloxyethoxycarbonylphthalic acid, 4-(meth) acryloyloxybutyloxycarbonylphthalic acid, 4-(meth) acryloyloxyhexyloxycarbonylphthalic acid, 4-(meth) acryloyloxyoctyloxycarbonylphthalic acid, 4-(meth) acryloyloxydecyloxycarbonylphthalic acid, maleic acid, and an acid anhydride thereof, 5-(meth) acryloylaminopentylcarboxylic acid, 6-(meth)acryloyloxy-1,1-hexanedicarboxylic acid, 7-(meth)acryloyloxy-1,1-heptanedicarboxylic acid, 8-(meth)acryloyloxy-1,1-octanedicarboxylic acid, 10-(meth) acryloyloxy-1,1-decanedicarboxylic acid, 11-(meth)acryloyloxy-1,1-undecanedicarboxylic acid and the like and, furthermore, acid chlorides, alkali metal salts, alkaline earth metal salts and ammonium salts thereof.

Among the acidic group-containing polymerizable monomer in the present invention, examples of the monomer containing a phosphoric ester group, a phosphonic acid group, or a pyrophosphoric acid group in the molecule include polymerizable monomers such as 3-(meth)acryloxypropyl-3-phosphonopropionate, 3-(meth)acryloxypropyl-3-phosphonoacetate, 4-(meth)acryloxybutyl-3-phosphonopropionate, 4-(meth) acryloxybutylphosphonoacetate, 5-(meth)acryloxypentylphosphono-3-propionate, 5-(meth)acryloxypentyl-3-phosphonoacetate, 6-(meth)acryloxyhexyl-3-phosphonopropionate, 6-(meth)acryloxyhexyl-3-phosphonoacetate, 10-(meth)acryloxydecyl-3-phosphonopropionate, 10-(meth) acryloxydecyl-3-phosphonoacetate, bis[2-(meth)acryloxyethyl]phosphate, (meth) acryloyloxyethyldihydrogenphosphate, 3-(meth) acryloyloxypropyldihydrogenphosphate, 4-(meth) acryloyloxybutyldihydrogenphosphate, 5-(meth) acryloyloxypentyldihydrogenphosphate, 6-(meth)acryloyloxyhexyldihydrogenphosphate, 7-(meth)acryloyloxyheptyldihydrogenphosphate, 8-(meth) acryloyloxyoctyldihydrogenphosphate, 9-(meth) acryloyloxynonyldihydrogenphosphate, 10-(meth)acryloyloxydecyldihydrogenphosphate, 11-(meth) acryloyloxyundecyldihydrogenphosphate, 12-(meth) acryloyloxydodecyldihydrogenphosphate, 11-(meth)acryloyloxyhexadecyldihydrogenphosphate, 20-(meth)acryloyloxyeicosyldihydrogenphosphate, di[2-(meth) acryloyloxyethyl]hydrogenphosphate, di[4-(meth) acryloyloxybutyl]hydrogenphosphate, di[6-(meth) acryloyloxyhexyl]hydrogenphosphate, di[8-(meth) acryloyloxyoctyl]hydrogenphosphate, di[9-(meth) acryloyloxynonyl]hydrogenphosphate, di[10-(meth) acryloyloxydecyl]hydrogenphosphate, 1,3-di(meth)acryloxyoxypropyl-2-dihydrogenphosphate, 2-(meth)acryloyloxyethylphenylhydrogenphosphate, 2-(meth) acryloyloxyethyl 2-bromoethylhydrogenphosphate, 2-(meth) acryloyloxyethyl phenylphosphonate, 10-(meth) acryloyloxydecylphosphonic acid, vinylphosphonic acid, and p-vinylbenzylphosphonic acid, as well as 2-methacryloyloxyethyl (4-methoxyphenyl)hydrogenphosphate, 2-methacryloyloxypropyl(4-methoxyphenyl)hydrogenphosphate, di[2-(meth) acryloyloxyethyl]pyrophosphate, di[4-(meth)acryloyloxybutyl]pyrophosphate, di[6-(meth) acryloyloxyhexyl]pyrophosphate, di[8-(meth) acryloyloxyoctyl]pyrophosphate, di[10-(meth)acryloyloxydecyl]pyrophosphate and the like described in JP-A No. 62-281885 and, furthermore, acid chlorides, alkali metal salts, alkaline earth metal salts and ammonium salts thereof.

Among the acidic group-containing polymerizable monomer in the present invention, examples of the monomer having a sulfonic acid group in the molecule include styrenesulfonic acid, 2-sulfoethyl (meth)acrylate, 6-sulfohexyl (meth)acrylate, 10-sulfodecyl (meth)acrylate, 2-(meth)acrylamide-2-methylpropanesulfonic acid and the like and, furthermore, acid chlorides, alkali metal salts, alkaline earth metal salts and ammonium salts thereof.

Among the acidic group-containing polymerizable monomer in the present invention, a preferable polymerizable monomer is a (meth)acrylate-based monomer containing a phosphonic acid group represented by:

[Chemical Formula 19]

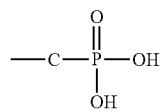

In the present invention, "(meth)acrylate" means acrylate or methacrylate. Preferable examples include (meth)acrylate represented by the following general formula

[Chemical Formula 20]

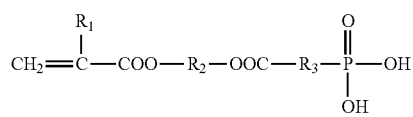

[1]

(wherein $R_1$ denotes a hydrogen atom or a methyl group, $R_2$ denotes an alkylene group of a carbon number of 1 to 20 optionally having a substituent, and $R_3$ denotes an alkylene group of a carbon number of 1 to 15 optionally having a substituent).

Examples of the alkylene group include those described for the general formula [1]. Herein, as a substituent which may bind to $R_2$ or $R_3$, there are unsaturated groups such as an alkenyl group and an alkynyl group, an alkyl group, and an alkyl group bound to a phenyl group.

Examples of the alkenyl group include:

[Chemical Formula 21]

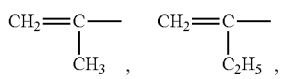

examples of the alkyl group include —$CH_3$, —$C_2H_5$, and —$C_3H_7$, and examples of the alkyl group bound to a phenyl group include —$CH_2CH_2OC_6H_5$. Examples of a specific compound represented by the general formula [1] include the following compounds:

[Chemical Formula 22]

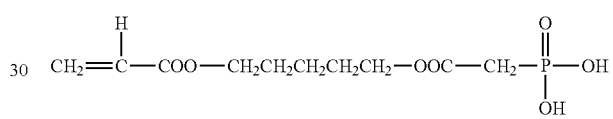

[Chemical Formula 23]

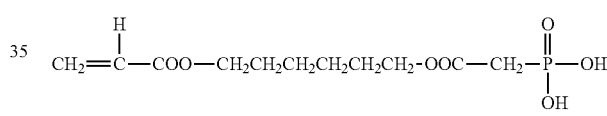

[Chemical Formula 24]

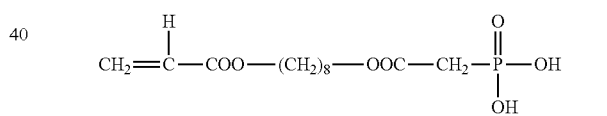

[Chemical Formula 25]

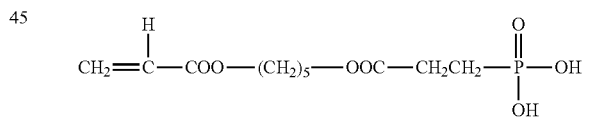

[Chemical Formula 26]

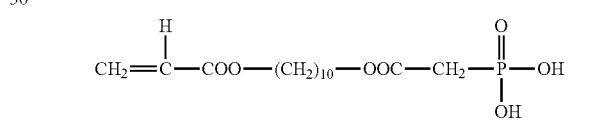

[Chemical Formula 27]

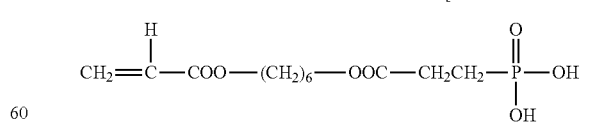

[Chemical Formula 28]

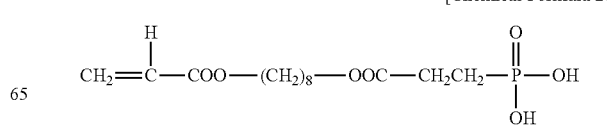

-continued

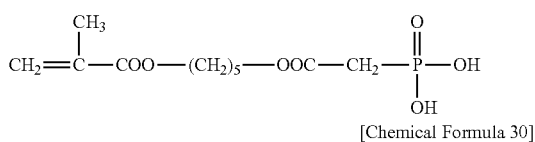
[Chemical Formula 29]

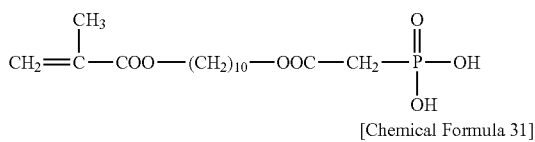
[Chemical Formula 30]

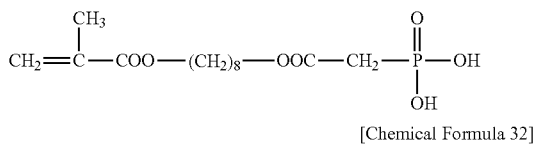
[Chemical Formula 31]

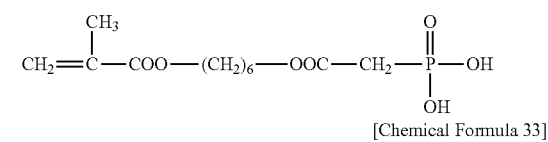
[Chemical Formula 32]

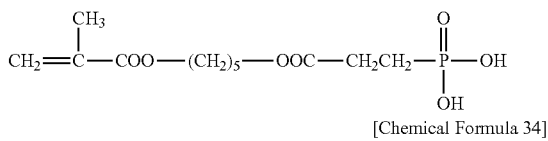
[Chemical Formula 33]

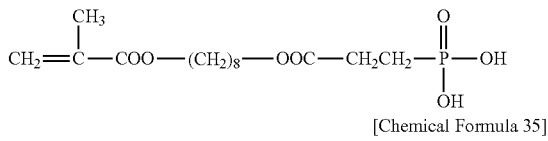
[Chemical Formula 34]

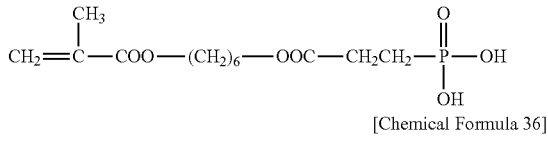
[Chemical Formula 35]

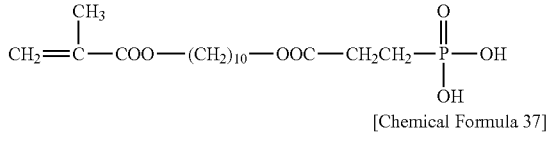
[Chemical Formula 36]

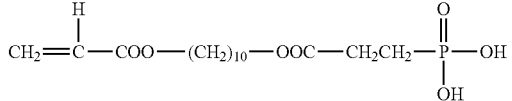
[Chemical Formula 37]

A particularly preferable phosphonic acid group-containing (meth)acrylate-based monomer is 6-methacryloxyhexyl-phosphonoacetate, 6-methacryloxyhexyl-3-phosphonopropionate, 10-methacryloxydecyl-3-phosphonopropionate, and 10-methacryloxydecyl-phosphonoacetate, and a particularly preferable phosphonic acid group-containing (meth)acrylate-based monomer is 6-methacryloxyhexyl-phosphonoacetate or 6-methacryloxyhexyl-3-phosphonopropionate.

A blending ratio of (b) the acidic group-containing polymerizable monomer may appropriately vary depending on the use purpose of the composition, and is adjusted in the range of 1.0 to 20.0 parts by weight, preferably is adjusted in the range of 4.0 to 15.5 parts by weight based on 100 parts by weight of (a) the silane coupling agent.

(c) The volatile organic solvent in the present invention is methanol, ethanol, isopropanol, butanol, acetone, ethyl acetate, and isopropyl ether, as well as a radical-polymerizable monomer such as (meth)acrylic acid ester, (meth)acrylamide, vinyl ester and the like;

Preferable is ethanol, and acetone, and a blending ratio of (c) the volatile organic solvent may appropriately vary depending on the use purpose of the composition, and is adjusted in the range of 28 to 99 parts by weight, preferably is adjusted in the range of 42.25 to 94.8 parts by weight.

The dental adhesive composition of the present invention contains, as an essential component, (a) the silane coupling agent, (b) the acidic group-containing polymerizable monomer, and (c) the volatile organic solvent, other components may be selected and added appropriately thereto, and addition components, that is, a radical polymerizable monomer, a photopolymerization initiator, a photopolymerization promoter, a thermal polymerization initiator, a polymerization catalyst, an inorganic and organic filler, a polymerization inhibitor, and a pigment may be appropriately incorporated therein, depending on the utility.

The radical polymerizable monomer can be added to the dental adhesive composition of the present invention. Examples of the radical polymerizable monomer include (meth)acrylates such as (meth)acrylic acid, methyl (meth) acrylate, and ethyl (meth)acrylate, and (meth)acrylates having an alkyl side chain substituted with a hydroxy group and a halogen, methoxydiethylene glycol (meth)acrylate, methoxypolyethylene glycol (meth)acrylate, ethylene glycol di(meth)acrylate, triethylene glycol di(meth)acrylate, tetraethylene glycol di(meth)acrylate, hexamethylene glycol di(meth)acrylate, polyethylene glycol di(meth)acrylate, propylene glycol di(meth)acrylate, polypropylene glycol di(meth)acrylate, neopentyl glycol di(meth)acrylate, 2,2'-bis{4-(meth)acryloxypropoxyphenyl}propane, 2,2'-bis{4-(meth)acryloxyethoxyphenyl}propane, 2,2'-bis{4-(meth) acryloxydiethoxyphenyl}propane, bisphenol di(meth) acrylate, bisphenol A diglycidyl (meth)acrylate, trimethylolpropane tri(meth)acrylate, trimethylolethane tri (meth)acrylate, tetramethylolethane tetra(meth)acrylate, epoxy-(meth)acrylate, urethane (meth)acrylates which are reaction products of organic diisocyanates and oxyalkyl (meth)acrylates, polymerizable prepolymers which are reaction products of urethane prepolymers (reaction product of organic diisocyanate and diol) and (meth)acrylic acid ester of oxyalkanol having at least two carbon atoms, and contain at least two polymerizable ethylenic unsaturated groups, and reaction products of dibasic carboxylic acid having an ethylenic unsaturated group and a dihydric alcohol (i.e. generally polyester having ethylenic unsaturated group).

These radical polymerizable monomers are used alone, or by appropriately combining them and, inter alia, a combination of bisphenol A diglycidyl (meth)acrylate of a polymerizable monomer such as di(meth)acrylate and the like, and triethylene glycol di(meth)acrylate is preferable.

As the polymerization initiator used in the present invention, the known compounds which are generally used in dental compositions are used without any limitation. The polymerization initiator is generally classified into a thermal polymerization initiator and a photopolymerization initiator.

As the photopolymerization initiator, a photosensitizer generating a radical by light irradiation can be used. Examples of the photosensitizer for ultraviolet ray include benzoin compounds such as benzoin, benzoin methyl ether, benzoin ethyl ether and the like, benzophenone-based compounds such as acetoin benzophenone, p-chlorobenzophenone, p-methoxybenzophenone and the like, and thioxanthone compounds such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, 2,4-diisopropylthioxanthone and the like. In addition, since a photosensitizer which initiates polymerization with visible light does not need ultraviolet-ray which is harmful to a human body, it is suitably used. Examples thereof include a-diketones such as benzil, camphorquinone, a-naphthil, acetonaphthene, p,p'-dimethoxybenzil, p,p'-dichlorobenzylacetil, pentanedione, 1,2-phenanthrenequinone, 1,4-phenanthrenequinone, 3,4-phenanthrenequinone, 9,10-phenanthrenequinone, naphthoquinone and the like. Preferably, camphorquinone is used.

Alternatively, it is also preferable to use a combination of the photosensitizer with a photopolymerization promoter. Particularly, when tertiary amines are used as the photopolymerization promoter, it is more preferable to use a compound in which an aromatic group is directly substituted with a nitrogen atom. As such the photopolymerization promoter, tertiary amines such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N,N-dimethylaniline, m-chloro-N,N-dimethylaniline, dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, N,N-dihydroxyethyl-p-toluidine, p-dimethylaminophenyl alcohol, p-dimethylaminostyrene, N,N-dimethyl-3,5-xylidine, 4-dimethylaminopyridine, N,N-dimethyl-a-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, 2,2'-(n-butylimino)diethanol and the like, barbituric acids such as 5-butylbarbituric acid, 1-benzyl-5-phenylbarbituric acid and the like, and metal salts thereof such as a sodium salt, and a calcium salt, and tin compounds such as dibutyl-tin-diacetate, dibutyl-tin-dimaleate, dioctyl-tin-dimaleate, dioctyl-tin-dilaurate, dibutyl-tin-dilaurate, dioctyl-tin-diversatate, dioctyl-tin-S,S'-bis-isooctylmercaptoacetate, tetramethyl-1,3-diacetoxydistannoxane and the like can be used. Of these photopolymerization promoters, at least one kind can be selected and used, and two or more kinds may be used by mixing them. An addition amount of the initiator and the promoter can be appropriately determined.

Further, in order to improve the photopolymerization promoting ability, in addition to tertiary amine, it is effective to add oxycarboxylic acids such as citric acid, malic acid, tartaric acid, glycolic acid, glucuronic acid, a-oxyisobutyric acid, 2-hydroxypropanoic acid, 3-hydroxypropanoic acid, 3-hydroxybutanoic acid, 4-hydroxybutanoic acid, dimethylolpropionic acid and the like.

To specifically exemplify the thermal polymerization initiator, organic peroxides such as benzoyl peroxide, parachlorobenzoyl peroxide, 2,4-dichlorobenzoyl peroxide, acetyl peroxide, lauroyl peroxide, tertiary butyl peroxide, cumene hydroperoxide, 2,5-dimethylhexane-2,5-dihydroperoxide, methyl ethyl ketone peroxide, tertiary butyl peroxybenzoate and the like, and azo compounds such as azobisisobutyronitrile, methyl azobisisobutyrate, azobiscyanovaleric acid and the like are suitably used.

Alternatively, by using the organic peroxide and an amine compound by combining them, polymerization may be performed at a normal temperature. As such the amine compound, secondary or tertiary amines in which an amine group is bound to an aryl group are more preferably used from a viewpoint of curing promotion. For example, N,N-dimethyl-p-toluidine, N,N-dimethylaniline, N,N-β-hydroxyethylaniline, N,N-di(β-hydroxyethyl)-aniline, N,N-di(β-hydroxyethyl)-p-toluidine, N-methyl-aniline, and N-methyl-p-toluidine are preferable.

It is also preferable to combine the combination of the organic peroxide and the amine compound, further with sulfinic acid salts or borate. Examples of such the sulfinic acid salts include sodium benzenesulfinate, lithium benzenesulfinate, sodium p-toluenesulfinate and the like. Examples of borate include a sodium salt, a lithium salt, a potassium salt, a magnesium salt, a tetrabutylammonium salt, and a tetramethylammonium salt of trialkylphenylboron, trialkyl(p-fluorophenyl)boron (alkyl group is n-butyl group, n-octyl group, n-dodecyl group etc.). Alternatively, organic boron compounds such as tributylborane, tributylborane partial oxides and the like which generate a radical by a reaction with oxygen or water may be used as an organic metal-type polymerization initiator.

The known various additives may be blended into the dental adhesive composition of the present invention as necessary. Examples of such the additives include a polymerization inhibitor, a coloring agent, a discoloration preventing agent, a fluorescent agent, a ultraviolet absorbing agent, an antibacterial agent and the like.

Examples of the inorganic and organic fillers include organic fillers obtained by grinding an organic polymer powder of polymethyl methacrylate, polyethyl methacrylate, a copolymer of methyl methacrylate and ethyl methacrylate, polystyrene and the like, or a cured product of a thermosetting resin, or a cured product of a thermosetting resin containing an inorganic filler, and inorganic fillers (kaolin, talc, quartz, silica, colloidal silica, alumina, aluminosilicate, silicon nitride, barium sulfate, calcium phosphate, barium sulfate, glass powder etc.), and composite fillers of an inorganic filler and an organic filler, and they are suitable for the composition to use as a powder/liquid type, a paste or a slurry. A surface of them may be covered with a coupling agent containing a silanol group (γ-methacryloxypropyltrimethoxysilane etc.).

Examples of the polymerization retarder include hydroquinone, hydroquinone monomethyl ester, butylated hydroxytoluene and the like, and is suitable for stabilizing a shelf life of the composition.

EXAMPLES

The following Examples and Comparative Examples specifically illustrate the present invention. But, the present invention is not limited by these Examples.

Abbreviations (chemical names) shown in Examples
1) Silane Coupling Agent
  3-MPDES: 3-Methacryloxypropylmethyldiethoxysilane
  3-MPTES: 3-Methacryloxypropyltriethoxysilane
2) Acidic Group-Containing Polymerizable Monomer
  6-MHPA: 6-Methacryloxyhexyl-phosphonoacetate
  6-MHPP: 6-Methacryloxyhexyl-3-phosphonopropionate
  10-MDPP: 10-Methacryloxydecyl-3-phosphonopropionate
  10-MDPA: 10-Methacryloxydecyl-phosphonoacetate
3) Radical Polymerizable Monomer
  Bis-GMA: Bisphenol A diglycidyl methacrylate
  3G: Triethylene glycol dimethacrylate
4) Photopolymerization Initiator, Photopolymerization promoter
  CQ: Camphorquinone DMDE:
5) Filler
R-972: Fine particle silicic acid [manufactured by Japan Aerosil Co., Ltd.]

(Materials and Apparatuses Used in Experiments)

Resin cement: "IMPERVA DUAL" [manufactured by Shofu]

Aluminum oxide plate: about 15×15×2 mm [manufactured by Japan Fine Ceramics Co., Ltd.]

Zirconium oxide plate: about 15×15×2 mm [manufactured by Japan Fine Ceramics Co., Ltd.]

Porcelain disk-like plate: diameter 15.0×5.0 mm [porcelain for baking dental metal [trade name "Vintage Hello" (manufactured by Shofu)]]

Thermal cycle tester: [manufactured by Tokyo Giken Inc.]

Instron universal tester [manufactured by Instron]

Examples 1 to 20 and Comparative Examples 1 to 5

Examples of Dental Primers or Dental Adhesives

As an example of a dental ceramics material consisting of aluminum oxide or a zirconium oxide, employing an aluminum oxide plate (about 15×15×2 mm [manufactured by Japan Fine Ceramics Co., Ltd.]) and a zirconium oxide plate (about 15×15×2 mm [manufactured by Japan Fine Ceramics Co., Ltd.]), a tensile adhesion strength test was performed. An adhesive composition was prepared by mixing at a weight ratio shown in Tables 1 to 3.

A flat surface of an aluminum oxide or zirconium oxide plate of about 15×15×2 mm was polished with a No. 240, then, No. 600 silicon carbide paper [manufactured by Sankyo Rigaku Co., Ltd.] under running water to obtain a smooth surface, the smooth surface was subjected to air ablation (50 μm alumina beads, 2.5 kgf/cm$^2$ pressure), and ultrasound-washed and air-dried to obtain an adherend. An adhesive composition was coated on an adhesive surface of the adherend with a mini-brush, this was as it was allowed to stand for 30 seconds, and dried with an air syringe to such an extent that fluidity of the adhesive composition disappeared. Separately, an adhesive surface of a cylindrical stainless bar of diameter 5 mm×height 10 mm was subjected to air ablation (50 μm alumina beads, 5 kgf/cm$^2$ pressure) and, thereafter, the surface was ultrasound-washed and air-dried to obtain a jig for measuring an adhesion strength. Adhesion was performed while "IMPERVA DUAL" which had been uniformly kneaded into a paste intervened between an adhesive surface of the adherend and an adhesive surface of a stainless bar. Thereupon, an extra cement was removed with a mini-brush, and photopolymerization was performed for 10 seconds using "Shofu Grip Light II" in a cement margin. All seven test pieces were immersed in water at 37° C. and, after immersion in water 37° C. for 24 hours, a tensile adhesion strength was measured. For measuring an adhesion strength, a tensile adhesion strength was measured using a universal tester (manufactured by Instron) under the condition of a crosshead speed of 1 mm/min. All adhesion tests were performed at room temperature of 23° C.±1° C.

Herein, a tensile adhesion strength when an adhesive composition was prepared by blending and mixing at a weight ratio shown in Tables 1 to 4, and this was brought into the sealed state, and was used under storage environment at 23° C. within 24 hours was adopted as an "initial" tensile adhesion strength. In addition, a tensile adhesion strength when an adhesive composition was prepared by blending and mixing at a weight ratio shown in Tables 1 to 4, and this was brought into the sealed state, and was used after storage for 2 months under storage environment at 50° C. was adopted as tensile strength "after 50° C. 2 months storage".

As an example of a dental ceramics material containing silicon dioxide as a main component, a porcelain for baking a dental metal [trade name "Vintage Hello" (manufactured by Shofu)] was employed, and a disk-like (diameter 15.0×5.0 mm) fired product was prepared using a vacuum electric furnace for firing a porcelain [trade name "Twin Mat" (manufactured by Shofu)], and a tensile adhesion strength test was performed. An adhesive composition was prepared by mixing at a weight ratio shown in Tables 1 to 3.

A flat surface of a disk-like (diameter 15.0×5.0 mm) fired product was polished under running water using a No. 240, then, No. 600 silicon carbide paper [manufactured by Sankyo Rigaku Co., Ltd.] to obtain a smooth surface, and this was ultrasound-washed and air-dried to obtain an adherend. An adhesive composition was coated on an adhesive surface of the adherend with a mini-brush, and this was as it was allowed to stand for 30 seconds, and dried with an air syringe to such an extent that fluidity of the adhesive composition disappeared. Separately, an adhesive surface of a cylindrical Cobaltan (cobalt chromium alloy: manufactured by Shofu) bar of diameter 5 mm×height 10 mm was subjected to air ablation (50 μm alumina beads, 5 kgf/cm$^2$ pressure) and, thereafter, was ultrasound-washed and air-dried to obtain a jig for measuring an adhesion strength. Adhesion was performed while "IMPERVA DUAL" which had been uniformly kneaded into a paste intervened between an adhesive surface of an adherend and an adhesive surface of a stainless bar. Thereupon, an extra cement was removed with a mini-brush, and photopolymerization was performed for 10 seconds using "Shofu Grip Light II" in a cement margin. All seven test pieces were immersed in water at 37° C. and, after immersion in water at 37° C. for 24 hours, a tensile adhesion strength was measured. For measuring an adhesion strength, a tensile adhesion strength was measured using a universal tester (manufactured by Instron) under the condition of a crosshead speed of 1 mm/min. All adhesion tests were performed at room temperature of 23° C.±1° C.

Herein, a tensile adhesion strength when an adhesive composition was prepared by blending and mixing at a weight ratio shown in Tables 1 to 4, and this was brought into the sealed state, and was used under storage environment at 23° C. within 24 hours was adopted as an "initial" tensile adhesion strength. In addition, a tensile adhesion strength when an adhesive composition was prepared by blending and mixing at a weight ratio shown in Tables 1 to 4, and this was brought into the sealed state, and was used after storage for 2 months under storage environment at 50° C. was adopted as tensile strength "after 50° C. 2 months storage".

Regarding Examples 1 to 5 and Comparative Examples 1 to 2, a blending amount of (a) the silane coupling agent was set to be 40 parts by weight, and a blending amount of (b) the acidic group-containing polymerizable monomer varied, in the adhesive compositions and, as apparent in comparison between Comparative Example 1 and Examples 1 to 5, adhesion with a porcelain, or alumina or zirconia is dramatically improved by the effect of blending (b) the acidic group-containing polymerizable monomer. However, as apparent in comparison between Comparative Example 2 and Examples 1 to 5, by increasing a blending amount of (b) the acidic group-containing polymerizable monomer based on 100 parts by weight of (a) the silane coupling agent from 18.6 parts by weight to 24.8 parts by weight, adhesion with a porcelain after storage at 50° C. for 2 months is remarkably reduced.

In addition, as apparent from Examples 6 to 9 and Comparative Examples 3 to 4, by increasing a blending amount of (b) the acidic group-containing polymerizable monomer to 24.8 parts by weight, the effect of remarkably reducing adhesion with a porcelain after storage at 50° C. for 2 months does not depend on a blending amount of (a) the silane coupling agent, but is determined by a ratio between both of them.

That is, as apparent from results of Examples 1 to 11, adhesion with a porcelain, or alumina or zirconia of the adhesive composition in which a blending amount of (b) the acidic group-containing polymerizable monomer based on 100 parts by weight of (a) the silane coupling agent is adjusted in the range of 1.6 to 18.6 parts by weight, is dramatically improved as compared with adhesion of a composition in which no (b) acidic group-containing polymerizable monomer is blended, and storage stability when formulated into a one-component composition is also better.

In addition, as apparent from Examples 10 to 12, also in a composition in which a blending amount of (a) the silane coupling agent is further increased, adhesion with a porcelain, or alumina or zirconia of an adhesive composition in which a blending amount of (b) the acidic group-containing polymerizable monomer based on 100 parts by weight of (a) the silane coupling agent is adjusted in the range of 1.6 to 18.6 parts by weight is better, and storage stability when formulated into a one-component composition is also better.

As apparent from Examples 13 to 15, also in a composition in which a phosphonic acid group-containing (meth)acrylate-based monomer is used as the acidic group-containing polymerizable monomer, and a blending amount of (a) the silane coupling agent is further increased, adhesion with a porcelain, or alumina or zirconia of an adhesive composition in which a blending amount of (b) the acidic group-containing polymerizable monomer based on 100 parts by weight of (a) the silane coupling agent is adjusted in the range of 1.6 to 18.6 parts by weight is better, and storage stability when formulated into a one-component composition is also better.

Examples 16 to 20 are an adhesive composition containing a radical polymerizable monomer and a photopolymerization initiator in the composition, and adhesion with a porcelain, or alumina or zirconia of an adhesive composition in which a blending amount of (b) the acidic group-containing polymerizable monomer based on 100 parts by weight of (a) the silane coupling agent is adjusted in the range of 1.6 to 18.6 parts by weight is better, and storage stability when formulated into a one-component composition is also better.

Industrial Applicability

As described above, according to the present invention, one-component dental adhesive composition which can exhibit excellent adhesion and durability on any material of a dental ceramics, and an organic composite containing an inorganic compound, and is excellent in can-stability can be provided.

TABLE 1

| | | | Comparative Example 1 | Example 1 | Example 2 | Example 3 | Example 4 | Example 5 | Comparative Example 2 | Comparative Example 3 |
|---|---|---|---|---|---|---|---|---|---|---|
| Blending amount of (a), (b) and (c) components [part by weight], and blending component name | (a) Silane coupling agent | 3MPTES | 40.0 | 40.0 | 40.0 | 40.0 | 40.0 | 40.0 | 40.0 | 4.00 |
| | (b) Acidic group-containing polymerizable monomer | 6-MHPA | | 0.64 | 1.64 | 2.48 | 4.96 | 7.44 | 9.92 | 0.99 |
| | (c) Volatile organic solvent | Acetone | 60.00 | 29.68 | 58.36 | 28.76 | | 52.56 | 50.08 | 95.01 |
| | | Ethanol | | 29.68 | | 28.76 | 55.04 | | | |
| Total of (a), (b) and (c) components blending amounts [part by weight] | | | 100.0 | 100.0 | 100.0 | 100.0 | 100.0 | 100.0 | 100.0 | 100.0 |
| Blending amount of (b) component based on 100 parts by weight of (a) component [part by weight] | | | 0.0 | 1.6 | 4.1 | 6.2 | 12.4 | 18.6 | 24.8 | 24.8 |
| Tensile adhesion strength [MPa] | Porcelain | Initial | 9.5 | 15.8 | 29.5 | 21.9 | 30.0 | 24.2 | 25.0 | 22.1 |
| | | After storage at 50° C. for 2 months | 9.3 | 14.5 | 22.4 | 20.0 | 26.9 | 17.1 | 9.3 | 8.5 |
| | Alumina | After storage at 50° C. for 2 months | 10.2 | 16.4 | 19.0 | 17.9 | 17.1 | 20.3 | 17.3 | 18.7 |
| | Zirconia | After storage at 50° C. for 2 months | 7.6 | 18.9 | 14.6 | 16.4 | 13.2 | 15.8 | 14.8 | 15.9 |

TABLE 2

| | | | Example 6 | Example 7 | Comparative Example 4 | Example 8 | Example 9 | Example 10 | Example 11 | Example 12 |
|---|---|---|---|---|---|---|---|---|---|---|
| Blending amount of (a), (b) and (c) components | (a) Silane coupling agent | 3MPTES | 4.00 | 4.00 | 20.00 | 20.00 | 20.00 | 50.00 | 50.00 | 60.00 |

TABLE 2-continued

|  |  |  | Example and Comparative Example |  |  |  |  |  |  |  |
|---|---|---|---|---|---|---|---|---|---|---|
|  |  |  | Example 6 | Example 7 | Comparative Example 4 | Example 8 | Example 9 | Example 10 | Example 11 | Example 12 |
| [part by weight], and blending component name | (b) Acidic group-containing polymerizable monomer | 6-MHPA | 0.25 | 0.06 | 4.96 | 1.24 | 0.32 | 6.20 | 2.05 | 3.72 |
|  | (c) Volatile Organic solvent | Acetone | 47.95 | 95.94 | 37.52 | 78.76 |  | 21.90 |  |  |
|  |  | Ethanol | 47.80 |  | 37.52 |  | 79.68 | 21.90 | 46.80 | 36.28 |
| Total of (a), (b) and (c) components blending amounts [part by weight] |  |  | 100.0 | 100.0 | 100.0 | 100.0 | 100.0 | 100.0 | 100.0 | 100.0 |
| Blending amount of (b) component based on 100 parts by weight of (a) component [part by weight] |  |  | 6.2 | 1.6 | 24.8 | 6.2 | 1.6 | 12.4 | 4.1 | 6.2 |
| Tensile adhesion strength [MPa] | Porcelain | Initial | 17.1 | 13.8 | 28.4 | 21.4 | 15.7 | 19.6 | 24.2 | 25.8 |
|  |  | After storage at 50° C. for 2 months | 12.1 | 13.1 | 9.5 | 15.7 | 15.5 | 16.5 | 25.6 | 25.6 |
|  | Alumina | After storage at 50° C. for 2 months | 17.7 | 16.6 | 16.7 | 17.9 | 16.5 | 18.7 | 16.5 | 21.6 |
|  | Zirconia | After storage at 50° C. for 2 months | 19.4 | 14.3 | 15.2 | 13.9 | 21.0 | 14.4 | 15.6 | 18.4 |

TABLE 3

|  |  |  | Example and Comparative Example |  |  |
|---|---|---|---|---|---|
|  |  |  | Example 13 | Example 14 | Example 15 |
| Blending amount of (a), (b) and (c) components [part by weight], and blending component name | (a) Silane coupling agent | 3MPTES | 40.00 | 40.00 | 40.00 |
|  | (b) Acidic group-containing polymerizable monomer | 6-MHPP | 3.72 |  |  |
|  |  | 10-MDPP |  | 3.72 |  |
|  |  | 10-MDPA |  |  | 3.72 |
|  | (c) Volatile Organic solvent | Acetone | 8.48 | 56.28 | 18.76 |
|  |  | Ethanol | 47.80 |  | 37.52 |
| Total of (a), (b) and (c) components blending amounts [part by weight] |  |  | 100.0 | 100.0 | 100.0 |
| Blending amount of (b) component based on 100 parts by weight of (a) component [part by weight] |  |  | 9.3 | 9.3 | 9.3 |
| Tensile adhesion strength [MPa] | Porcelain | Initial | 19.9 | 20.6 | 21.0 |
|  |  | After storage at 50° C. for 2 months | 16.9 | 17.2 | 15.6 |
|  | Alumina | After storage at 50° C. for 2 months | 19.4 | 18.0 | 19.3 |
|  | Zirconia | After storage at 50° C. for 2 months | 12.5 | 12.8 | 14.5 |

TABLE 4

|  |  |  | Example and Comparative Example |  |  |  |  |  |
|---|---|---|---|---|---|---|---|---|
|  |  |  | Example 16 | Example 17 | Example 18 | Example 19 | Example 20 | Comparative Example 5 |
| Blending amount of (a), (b) and (c) components [part by weight], and blending component name | (a) Silane coupling agent | 3MPTES | 33.17 | 28.6 | 9.6 | 20.0 | 15.0 | 4.00 |
|  | (b) Acidic group-containing polymerizable monomer | 6-MHPA | 2.06 | 2.1 | 0.6 | 1.8 | 0.5 | 0.03 |
|  | (c) Volatile organic solvent | Ethanol | 47.69 | 17.3 | 11.3 |  |  | 95.97 |

TABLE 4-continued

| | | Example 16 | Example 17 | Example 18 | Example 19 | Example 20 | Comparative Example 5 |
|---|---|---|---|---|---|---|---|
| Radical polymerizable monomer [part by weight] | Bis-GMA | 11.61 | 32.0 | | | | 0 |
| | UDMA | | | 50.0 | 45.5 | 51.3 | |
| | 3G | 4.98 | 14.5 | 20.0 | 29.2 | 29.2 | |
| Photopolymerization initiator [part by weight] | CQ | 0.25 | 0.25 | 0.50 | 0.25 | 0.50 | 0 |
| Photopolymerization promoter [part by weight] | DMBE | 0.25 | 0.25 | 0.50 | 0.25 | 0.50 | 0 |
| Filler [part by weight] | R-972 | 0.00 | 5.0 | 7.5 | 3.0 | 3.0 | 0 |
| Total of component blending amounts [part by weight] | | 100.00 | 100.0 | 100.0 | 100.0 | 100.0 | 100.0 |
| Blending amount of (b) component based on 100 parts by weight of (a) component [part by weight] | | 6.2 | 7.3 | 6.3 | 9.0 | 3.3 | 0.75 |
| Tensile adhesion strength [MPa] | Porcelain Initial | 15.7 | 17.8 | 16.5 | 15.6 | 18.1 | 9.3 |
| | After storage at 50° C. for 2 months | 13.5 | 18.5 | 16.6 | 14.5 | 17.9 | 9.7 |
| | Alumina Initial | 12.0 | 19.8 | 21.0 | 20.5 | 21.1 | 8.4 |
| | After storage at 50° C. for 2 months | 13.8 | 19.5 | 19.9 | 22.1 | 21.4 | 7.9 |
| | Zirconia Initial | 14.4 | 17.1 | 17.5 | 17.3 | 18.7 | 7.8 |
| | After storage at 50° C. for 2 months | 13.7 | 17.7 | 16.9 | 17.6 | 17.2 | 7.5 |

The invention claimed is:

1. A method of improving the adhesion of a porcelain, alumina or zirconia, comprising coating a surface of the porcelain, alumina or zirconia with a one-component dental primer comprising (a) a silane coupling agent, (b) an acidic group-containing polymerizable monomer, and (c) a volatile organic solvent, wherein the primer comprises 1 to 60 parts by weight of (a) the silane coupling agent, 1.0 to 20.0 parts by weight based on 100 parts by weight of the (a) component of (b) the acidic group-containing polymerizable monomer, and 28 to 99 parts by weight of (c) the volatile organic solvent, and wherein (b) the acidic group-containing polymerizable monomer is a phosphonic acid group-containing (meth)acrylate monomer, and the phosphonic acid group-containing (meth)acrylate monomer is represented by the following formula [1]:

[Chemical Formula 1]

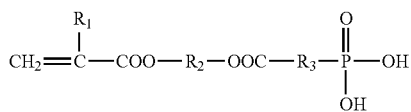

[1]

wherein $R_1$ denotes a hydrogen atom or a methyl group, $R_2$ denotes an alkylene group of a carbon atom number of 1 to 20 optionally having a substituent, and $R_3$ denotes an alkylene group of a carbon atom number of 1 to 15 optionally having a substituent.

2. A method of improving the adhesion of a porcelain, alumina or zirconia, comprising coating a surface of the porcelain, alumina or zirconia with a one-component dental adhesive comprising a radical polymerizable monomer, (a) a silane coupling agent, (b) an acidic group-containing polymerizable monomer, and a photopolymerization initiator, wherein (b) the acidic group-containing polymerizable monomer is 1.0 to 20.0 parts by weight based on 100 parts by weight of (a) the silane coupling agent, and wherein (b) the acidic group-containing polymerizable monomer is a phosphonic acid group-containing (meth)acrylate monomer, and the phosphonic acid group-containing (meth)acrylate monomer is represented by the following formula [1]:

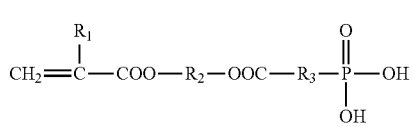

[1]

wherein $R_1$ denotes a hydrogen atom or a methyl group, $R_2$ denotes an alkylene group of a carbon atom number of 1 to 20 optionally having a substituent, and $R_3$ denotes an alkylene group of a carbon atom number of 1 to 15 optionally having a substituent.

* * * * *